United States Patent
Kligerman et al.

(10) Patent No.: US 7,402,323 B2
(45) Date of Patent: Jul. 22, 2008

(54) COMPOSITIONS AND METHODS FOR TREATING SKIN CONDITIONS

(75) Inventors: Alan E. Kligerman, Egg Harbor Township, NJ (US); Sarah Finnegan, Mays Landing, NJ (US); Margaret Weis, Amarillo, TX (US)

(73) Assignee: AkPharma, Inc., Pleasantville, NJ (US)

( * ) Notice: Subject to any disclaimer, the term of this patent is extended or adjusted under 35 U.S.C. 154(b) by 621 days.

(21) Appl. No.: 10/639,213

(22) Filed: Aug. 12, 2003

(65) Prior Publication Data

US 2004/0037766 A1 Feb. 26, 2004

Related U.S. Application Data

(60) Provisional application No. 60/405,078, filed on Aug. 21, 2002.

(51) Int. Cl.
*A01N 59/06* (2006.01)
*A01N 59/08* (2006.01)
*A61K 33/14* (2006.01)

(52) U.S. Cl. ............... 424/678; 424/682; 424/687; 514/880

(58) Field of Classification Search ............... 424/401, 424/682, 602, 686, 687, 639, 641, 647, 678
See application file for complete search history.

(56) References Cited

U.S. PATENT DOCUMENTS

| | | | |
|---|---|---|---|
| 2,118,566 A | 5/1938 | Miles | |
| 4,105,783 A | 8/1978 | Yu | |
| 4,197,316 A | 4/1980 | Yu | |
| 4,363,815 A | 12/1982 | Yu | |
| 4,380,549 A | 4/1983 | Van Scott | |
| 4,560,555 A | 12/1985 | Snider | |
| 4,588,590 A | 5/1986 | Bernstein | |
| 4,743,442 A | 5/1988 | Raaf et al. | |
| 4,772,591 A | 9/1988 | Meisner | |
| 4,797,481 A | 1/1989 | Garlisi | |
| 4,940,666 A | 7/1990 | Boyce et al. | |

(Continued)

FOREIGN PATENT DOCUMENTS

FR 2725901 A1 * 4/1996

OTHER PUBLICATIONS

Thorel Jean Noel, FR 27225901 A1, 1996.*

(Continued)

*Primary Examiner*—Johann Richter
*Assistant Examiner*—Konata M George
(74) *Attorney, Agent, or Firm*—Panitch Schwarze Belisario & Nadel LLP

(57) ABSTRACT

A skin treatment composition containing ionic calcium and a dermatologically acceptable water-soluble, water-miscible or water-based carrier is provided for treating a skin condition in a mammal, such as dry skin, dry scalp, a burn, sunburn, irritation or minor wound. The ionic calcium is preferably present as the water soluble calcium glycerophosphate salt. The composition may be present in a formulation such as bar soap, liquid soap, bath, lotion, cream, gel, or ointment, and may also be useful for stimulating more youthful skin cells and for improving the appearance of the skin. Methods for treating skin conditions and for accelerating cellular repair include topically applying to the skin an effective amount of ionic calcium, preferably as calcium glycerophosphate, and an α-hydroxy acid such as lactic acid.

13 Claims, 3 Drawing Sheets

U.S. PATENT DOCUMENTS

| | | | |
|---|---|---|---|
| 5,084,281 A | 1/1992 | Dillon | |
| 5,139,771 A | 8/1992 | Gerstein | |
| 5,194,253 A | 3/1993 | Garrido | |
| 5,292,655 A | 3/1994 | Wille, Jr. | |
| 5,593,682 A | 1/1997 | Papas et al. | |
| 5,602,183 A | 2/1997 | Martin et al. | |
| 5,618,529 A | 4/1997 | Pichierri | |
| 5,643,586 A | 7/1997 | Perricone | |
| 5,658,956 A | 8/1997 | Martin et al. | |
| 5,660,859 A | 8/1997 | Cody et al. | |
| 5,665,368 A | 9/1997 | Lentini et al. | |
| 5,716,625 A | 2/1998 | Hahn et al. | |
| 5,776,473 A | 7/1998 | Perricone et al. | |
| 5,830,507 A | 11/1998 | Armstrong | |
| 5,858,380 A | 1/1999 | Gagnebien | |
| 5,866,147 A | 2/1999 | Ptchelintsev | |
| 5,922,335 A | 7/1999 | Ptchelintsev | |
| 5,922,359 A * | 7/1999 | Youssefyeh | 424/570 |
| 5,958,436 A | 9/1999 | Hahn et al. | |
| 5,972,321 A | 10/1999 | Kligerman et al. | |
| 6,013,279 A | 1/2000 | Klett-Loch | |
| 6,063,406 A | 5/2000 | Hornack | |
| 6,080,425 A | 6/2000 | Miljkovic et al. | |
| 6,136,328 A | 10/2000 | Sebillotte-Arnaud et al. | |
| 6,168,798 B1 | 1/2001 | O'Halloran et al. | |
| 6,184,247 B1 | 2/2001 | Schneider | |
| 6,277,388 B1 | 8/2001 | Chevalier | |
| 6,287,548 B1 | 9/2001 | Biener | |
| 6,294,180 B1 | 9/2001 | Demars et al. | |
| 6,296,856 B1 | 10/2001 | Pineau et al. | |
| 6,329,343 B1 | 12/2001 | Leung et al. | |
| 6,331,307 B1 | 12/2001 | Sibillotte-Arnaud et al. | |
| 6,599,512 B1 | 7/2003 | Burnier | |
| 6,830,764 B2 * | 12/2004 | Inui et al. | 424/669 |

OTHER PUBLICATIONS

McKeehan et al., "Epidermal growth factor modulates extracellular Ca2+ requirement for multiplication of normal human skin fibroblasts"; *Experimental Cell Research*, 123(2):397-400 (Oct. 15, 1979).

Hawley-Nelson et al., "Optimized conditions for the growth of human epidermal cells in culture"; *Journal of Investigative Dermatology*, 75(2): 176-82 (Aug. 1980).

Dykes et al., "The effect of calcium on the initiation and growth of human epidermal cells"; *Archives of Dermatological Research*, 273(3-4): 225-31 (1982).

Price et al., "Approaches to enhance proliferation of human epidermal keratinocytes in mass culture"; *Journal of the National Cancer Institute*, 70(5):853-61 (May 1983).

O'Keefe et al., "Modulation of the epidermal growth factor receptor of human keratinocytes by calcium ion"; *Journal of Investigative Dermatology*, 81(3): 231-5 (Sep. 1983).

Stoll et al., "Control of the re-epithelialization of skin defects and burns"; *Deutsche Zeitschrift fur Mund-, Kiefer-, und Geisichts-Chirurgie*, 13(4):260-5 (Jul.-Aug. 1989).

Michel et al., "Fibrin seal in wound healing: effect of thrombin and [Ca2+] on human skin fibroblast growth and collagen production"; *Journal of Dermatological Science*, 1(5): 325-33 (Sep. 1990).

Davey, et al., "Unusual donor site reactions to calcium alginate dressings"; *Burns*, 26(4):393-8 (Jun. 2000).

Sun et al., "CLED: A calcium-linked protein associated with early epithelial differentiation"; *Experimental Cell Research 259*, No. 1 (2000): 96-106 (Aug. 25, 2000).

McNeil et al., "Coping with the inevitable: How cells repair a torn surface membrane"; *Nature Cell Biology* 3, No. 5 (2001): E124-E129 (May 2001).

D'Souza et al., "Ca2+ and BMP-6 signaling regulate E2F during epidermal keratinocyte differentiation"; *Journal of Biological Chemistry* 276, No. 26 (2001: 23531-23538 (Jun. 29, 2001).

Reddy et al., "Plasma membrane repair is mediated by Ca2+-regulated exocytosis of lysosmes"; *Cell* 106, No. 2 (2001): 157-169 (Jul. 27, 2001).

Maziere, et al., "UVA Radiation Stimulates Ceramide Production: Relationship to Oxidative Stress and Potential Role in ERK, JNK, and p38 Activation," *Biochemical and Biophysical Research Communications*, 281(2):289-294, 2001.

Rawlings, et al., "Effect of lactic acid isomers on keratinocyte ceramide synthesis, stratum corneum lipid levels and stratum corneum barrier function," *Archives of Dermatological Research*, 288(7):383-390, 1996.

DiMarzio, et al., "Effect of the Lactic Acid Bacterium *Streptococcus thermophilus* on Ceramide Levels in Human Keratinocytes In Vitro and Statum Corneum In Vivo," *Journal of Investigative Dermatology*, 113(1):98-106, 1999.

Watanabe, et al., "Up-regulation of Glucosylceramide Synthase Expression and Activity during Human Keratinocyte Differentiation," *Journal of Biological Chemistry*, 273(16):9651-9655, 1998.

Ehlers, et al., "Females have lower skin surface pH than men," *Skin Research and Technology*, 7(2):90-94, 2001.

Runeman, et al., "Experimental *Candida albicans* Lesions in Healthy Humans: Dependence on Skin pH," *Acta Dermato-Venereologica* 80(6):421-424, 2000.

Oda, et al., "The Calcium Sensing Receptor and Its Alternatively Spliced Form in Murine Epidermal Differentiation," *Journal of Biological Chemistry*, 275(2):1183-1190, 2000.

Schmidt, et al., "Ras-independent Activation of the Raf/MEK/ERK Pathway upon Calcium-induced Differentiation of Keratinocytes," *Journal of Biological Chemistry*, 275(52):41011-41017, 2000.

"Skin Care Solutions", http://styles101.homestead.com/ahas.html.

"Cell-cell adhesion process", *University of Chicago Medical Center Office of Public Affairs Press Release* (2000).

Hahn et al., *Drug and Cosmetic Industry*, pp. 18-20, 22 (1998).

Tueson et al., *Am. Soc. Derm. Surg.* 24:641-645 (1998).

"Calcium Glycerophosphate", *National Academy of Sciences: Foods Chemical Codex IVth Ed.*, p. 60 (1996).

"Calcium Glycerophosphate", *Merck Index* $12^{th}$ *Edition*, p. 230 Monograph 1644 (1996).

* cited by examiner

COMPOSITIONS AND METHODS FOR TREATING SKIN CONDITIONS

CROSS-REFERENCE TO RELATED APPLICATION

This application claims the benefit of U.S. Provisional Patent Application No. 60/405,078, filed Aug. 21, 2002.

BACKGROUND OF THE INVENTION

The epidermis of humans and animals is composed of three layers: the stratum basale, the stratum spinosum and the stratum corneum, as best shown in FIG. 1. The stratum basale, the innermost layer, is the only layer in which active cell division occurs. When division transpires, a daughter cell, called a keratinocyte, begins to undergo terminal differentiation. By this process, the keratinocyte is sequentially transformed into a cell of the spinosum and then into one of the corneum. Among the changes occurring during differentiation are increased synthesis of ceramide, loss of the nucleus, cell death and replacement of the cytoplasm with keratin. As keratinocytes reach the outermost stratum corneum layer, they are shed to the environment.

The stratum corneum provides a mechanical barrier to the external environment, and the concentration of ceramide in this layer is directly correlated with moisture retention. Consequently, agents which increase ceramide content will also improve moisture retention. Further, acceleration of keratinocyte differentiation increases the turnover rate of the stratum corneum, thereby minimizing the appearance of excessively dry skin, known as xerosis.

The biochemical sequence of events in keratinocyte differentiation is complex and poorly understood. Regardless of the details, it appears that agents which induce the synthesis of ceramide (a sphingolipid), as shown in FIG. 2, are associated with the induction of keratinocyte differentiation. Such agents include UVA radiation (Maziere, et al. *Biochemical and Biophysical Research Communications*, 281(2):289-294, 2001), L-lactic acid (Rawlings, et al. *Archives of Dermatological Research*, 288(7):383-390, 1996), lactic acid bacteria (DiMarzio, et al. *Journal of Investigative Dermatology*, 113(1): 98-106, 1999) and extracellular calcium (Watanabe, et al, *J. Biol. Chem.*, 273 (16): 9651-5, 1998).

L-lactic acid, but not D-lactic acid, has recently been used as an effective treatment for xerosis. It is most likely efficacious because it promotes keratinocyte differentiation and ceramide synthesis (Rawling, et al; *Arch. of Derm. Res.*, 288 (7):383-90, 1996). The stereospecificity suggests that the action of L-lactic acid is not simply one of pH adjustment. Rather, the observation that the carbon label from L-lactic acid is incorporated into ceramide suggests that L-lactic acid provides an increased substrate for ceramide synthesis.

The normal pH of the stratum corneum is somewhat acidic, 5.80 in men and 5.54 in women (Ehlers, et al. *Skin Research and Technology*, 7(2):90-4, 2001). Maintenance of normal skin flora is pH dependent, and even modest increases in pH (0.1 to 0.2 pH units) are sufficient to foster growth of undesirable microorganisms such as *Candida albicans* (Runeman, et al. *Acta Dermato-Venereologica* 80(6): 421-4, 2000). Therefore, it is important that products designed for application to the skin have carefully controlled pH levels.

It has been found that the membranes of human keratinocytes possess a calcium-sensing protein that responds to increases in extracellular calcium, thereby initiating terminal differentiation (Oda, et al. *Journal of Biological Chemistry*, 275(2): 1183-90, 2000). Furthermore, researchers have shown that the addition of calcium to culture media will initiate in vitro differentiation in cultured human keratinocytes by activating a number of protein kinases, and calcium is thought to act very early in the differentiation process (Schmidt, et al. *Journal of Biological Chemistry*, 275(52): 41011-7, 2000).

Current methods for the stimulation of more youthful skin cells and for promoting the appearance of younger skin include skin peels, such as those utilizing glycolic acid. The pH of such peels may be as low as 2.0, a hydrogen ion concentration more than 3000 times greater than that measured on the surface of normal skin. Thus, it is not surprising that the use of glycolic acid peels may be accompanied by redness and irritation. Alternatively, retinoid compounds have been used topically for their ability to stimulate keratinocyte differentiation and promote collagen and elastin synthesis. However, they may also induce photosensitivity, limiting their utility in susceptible individuals.

For these reasons, there remains a need in the art for a method for stimulating more youthful looking skin without producing undesirable side effects, and which would also be useful for accelerating the healing of wounds without encouraging the growth of undesirable organisms such as *Candida albicans*.

BRIEF SUMMARY OF THE INVENTION

According to the present invention, a skin treatment composition comprising ionic calcium and a dermatologically acceptable water-based, water-soluble or water-miscible carrier is provided for the treatment of the skin of a mammal. The ionic calcium may be present in an amount effective to improve a condition or appearance of the skin, to stimulate more youthful skin cells, and/or to accelerate the healing of a wound or a burn. In a preferred embodiment, the ionic calcium is present as calcium glycerophosphate, and the composition further comprises a buffering agent. The skin treatment composition may be present in various forms or vehicles, such as a bar soap, a liquid soap, a shampoo, a bath, a cream, a gel, a lotion, an ointment or a powder. The calcium in the preferred calcium glycerophosphate is easily available in ionic form because the compound is highly soluable and becomes ionized instantly upon contact with water or an aqueous solution.

According to another embodiment of the invention, a method is provided for treating a skin condition of a mammal, such as dry skin, sunburn, other burns, dry scalp, or wound, which comprises applying to the skin an effective amount of ionic calcium. In a preferred embodiment, the method further comprises applying to the skin effective amounts of an α-hydroxy acid and a glycerophosphate moiety.

According to a further embodiment of the invention, a method for accelerating an internal cellular repair in the skin of a mammal involves applying to the skin of the mammal effective amounts of ionic calcium, glycerophosphate and α-hydroxy acid.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

Figure 1:
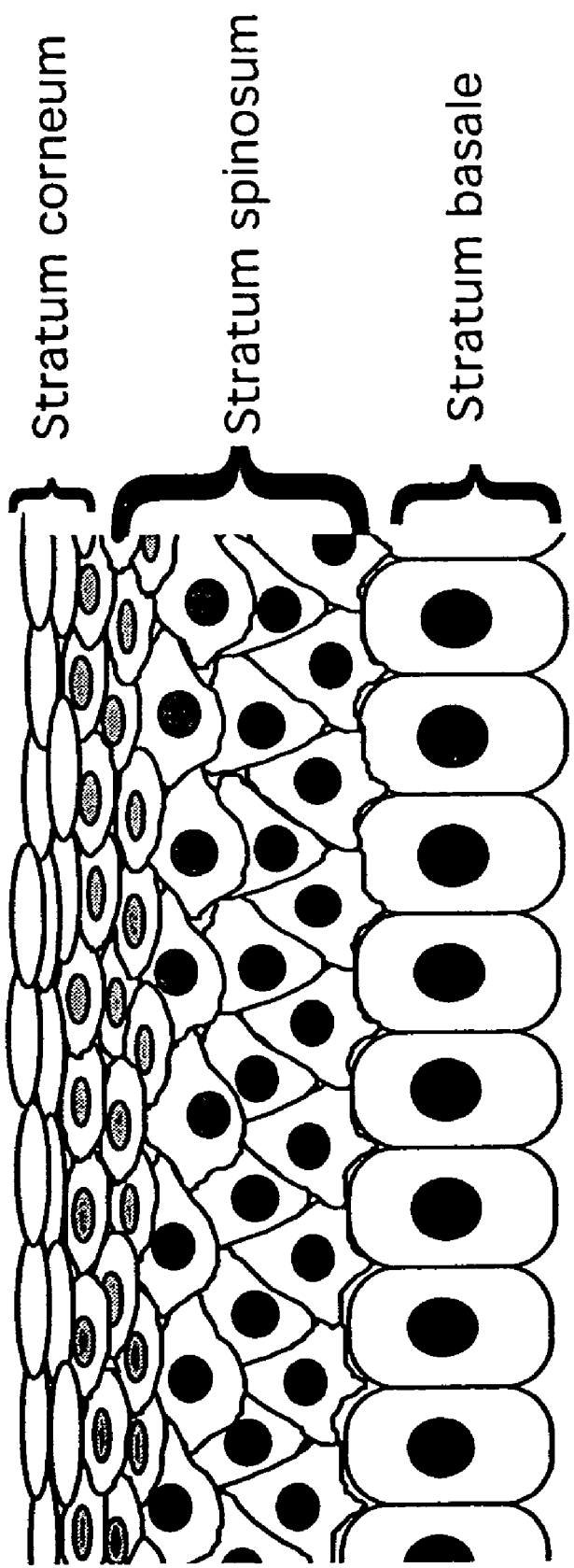
FIG. 1 is a schematic diagram depicting the three layers of the human and animal epidermis.
Figure 2:
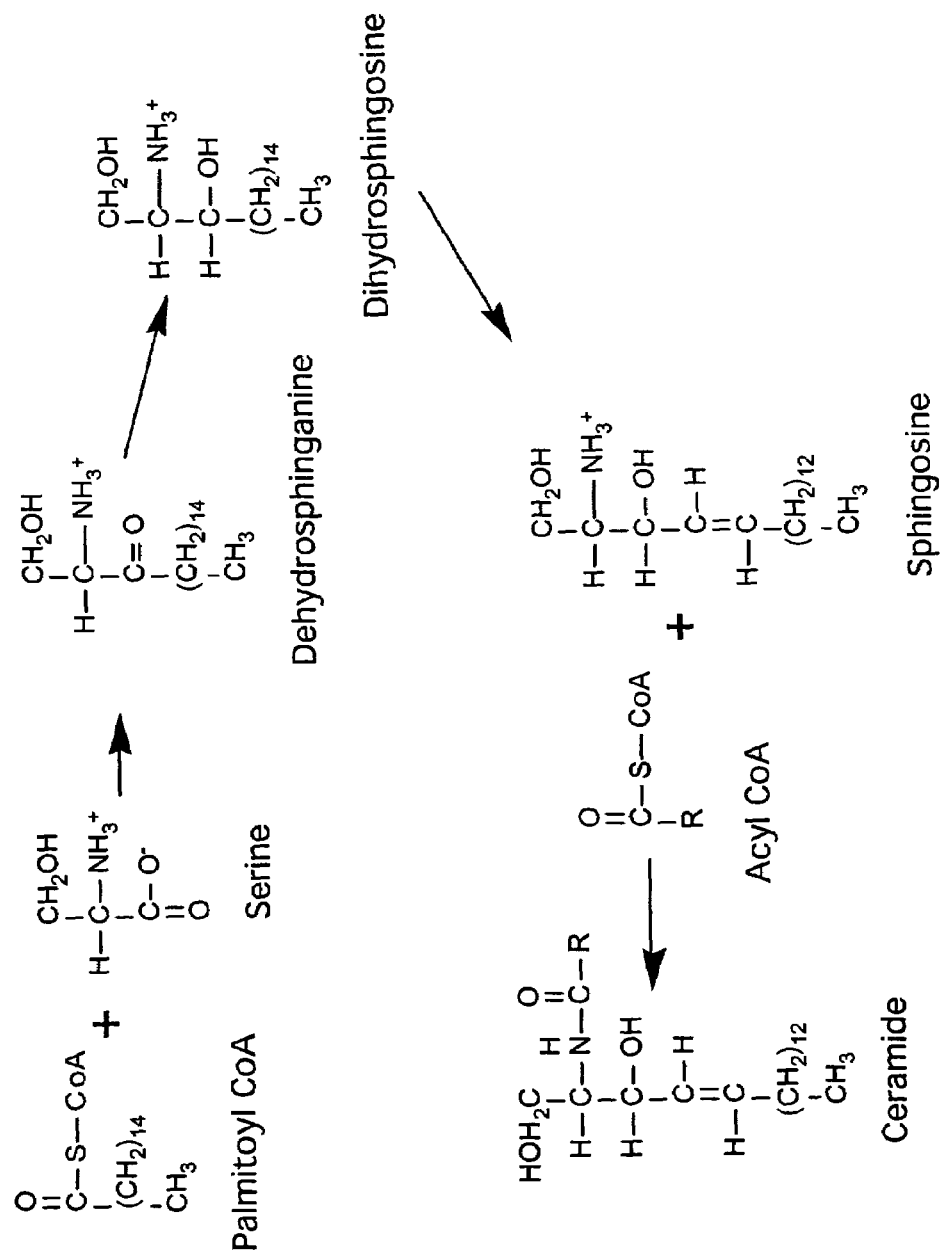
FIG. 2 is a diagram illustrating a reaction pathway of ceramide synthesis.

This invention is directed to skin treatment compositions containing ionic calcium for treating the skin of a mammal. The ionic calcium may be present in the compositions in an amount effective to improve the condition of the skin, to stimulate more youthful skin cells, and/or to improve the appearance of the skin. The effective amount of calcium in the compositions is preferably that which is sufficient to achieve concentrations of calcium in the extracellular fluid surrounding the cells of the *stratium basale* of about 0.01 to about 3 mM and more preferably about 0.03 to about 0.3 mM.

In order to achieve such concentrations, it may be necessary to apply greater amounts of calcium to the skin because some calcium may not be ionized, but may be absorbed into the blood, for example. As a result of transdermal absorption, the concentration of calcium on the outer surface of the skin will be greater than in the extracellular fluid present in the deeper tissues. Such a concentration gradient will cause calcium to diffuse into deeper skin layers and eventually to be absorbed by the blood thereby reducing the concentration available for ionization. Additionally, a percentage of the positively charges ionic calcium may be nonspecifically absorbed onto negatively charged proteins in the skin, and thus may not be available for binding specifically to the stratum basale cells as desired.

Therefore, in order to achieve the desired concentration of calcium in the fluid surrounding the cells of the *stratum basale*, it may be necessary to apply greater quantities of ionic calcium to the skin. The skin treatment compositions according to the present invention therefore preferably have a concentration of about 0.3 to about 5 mM calcium, and more preferably about 2 to about 5 mM. A preferred dosage for skin treatment comprises about 1 ml of skin treatment composition per about 100 cm² of skin.

Without wishing to be bound by theory, it is believed that the topical application of a composition containing ionic calcium, and preferably also glycerophosphate and an α-hydroxy acid, would stimulate keratinocyte differentiation and increase ceramide synthesis, thereby improving skin condition and appearance. As previously explained, the effect of external application of calcium has been demonstrated in vitro by Schmidt, et al. Similar effects on epidermal cells would be observed in vivo.

As skin ages, cell division in the stratum basale, the live, inner reproductive layer that feeds cells into the outer and protective keratinized layers, is less frequent, and there is reduced synthesis of ceramide. The reduced rate of replenishment of the stratum corneum, with its accompanying reduced rate of ceramide synthesis, contributes to the drier feeling and older appearance characteristic of aging skin. Acceleration of the transition from the stratum basale to the stratum corneum will help to minimize the appearance of aging. Such an acceleration may be induced by the topical application of ionic calcium, preferably accompanied by at least one α-hydroxy acid, such as lactic acid, and a glycerophosphate moiety. When applied topically to the skin, it is believed that the ionic calcium and α-hydroxy acid moiety would be absorbed through the stratum corneum and stratum spinosum layers of the epidermis and into the stratum basale.

The ionic calcium in the composition according to the present invention may be present in a water soluble inorganic salt, such as calcium carbonate or calcium chloride. The calcium may also be in the form of a water soluble organic salt, such as calcium lactate, calcium citrate, calcium gluconate, calcium ascorbate, calcium acetate, calcium maleate or calcium pantothenate. Preferably, the calcium is present as calcium glycerophosphate, which has the advantage of being highly soluble in water.

Calcium glycerophosphate (CGP) is also known as 1,2,3-propanetriol, mono(dihydrogen phosphate) calcium salt (1:1), calcium glycerinophosphate, calcium phosphoglycerate and NEUROSIN®. It has a molecular formula of $C_3H_7CaO_6P$ and a formula weight of 210.14 (anhydrous). It may exist as a hydrate, including the monohydrate and the dihydrate. Three CGP isomers exist, namely β-glycerophosphoric acid calcium salt $((HOCH_2)_2CHOPO_3Ca)$ and D(+) and L(−)-α-glycerophosphoric acid calcium salt $(HOCH_2CH(OH)CH_2OPO_3Ca)$. Any one isomer, or any combination of two or more isomers, may be used as the CGP according to this invention. A commercially available form of CGP is a mixture of calcium β- and DL-α-glycerophosphates, and this is a preferred form of CGP according to the invention. The preferred form of CGP is food grade CGP according to Food Chemicals Codex (FCC) III, and may be obtained from Astha Chemical Co., Hyderabad, India; Seppic Inc., Fairfield, NJ, as well as Gallard Schlesinger Company, Carl Place, N.Y. 11514, which is a distributor for the Dr. Paul Lohmann GmbH KG of Emmerthal, Germany.

It is known that calcium glycerophosphate has a hydrogen-ion binding capability, the means by which, in vivo and in vitro, CGP neutralizes the acid in foods and beverages and, topically applied, acidic conditions on the skin. The use of CGP to neutralize the acid in foods and beverages has been described in U.S. Pat. Nos. 5,665,415 and 5,869,119 of Kligerman, et al., which are herein incorporated by reference in their entirety. The use of CGP in neutralizing the acidity of skin is described in U.S. Pat. No. 5,972,321 of Kligerman, et al., which is also incorporated herein by reference.

In a preferred embodiment, the skin treatment composition further comprises a glycerophosphate moiety. The moiety may be added to the composition as glycerophosphoric acid or as a glycerophosphate salt. A preferred skin treatment composition comprises calcium glycerophosphate because it contains both ionic calcium and a glycerophosphate moiety and has favorable solubility properties. However, other glycerophosphate salts would also be within the scope of the invention, including sodium, potassium, zinc, magnesium, lithium, manganese, cupric, ferric and quinine glycerophosphates.

CGP is also the preferred source of calcium and glycerophosphate because it has been shown to be particularly effective on cultured cells. Specifically, Boucrout and Steinschneider ("Evaluation of the influence of calcium glycerophosphate on the cortical cells (astrocytes and neurons) in culture"; Laboratory of Immunopathology—University of Aix-Marseilles; Faculty of Medicine, 1995; and "Effect of calcium and magnesium glycerophosphates and glycerophosphoric acid and of calcium on the survival and differentiation of neurons of the rat, in culture"; University of Aix-Marseilles; Faculty of Medicine, 1996) studied the effect of calcium chloride, glycerophosphate alone and calcium glycerophosphate on cultured neurons and astrocytes. It was reported that there were more cells in the cultures supplemented with calcium glycerophosphate compared with control cultures or with cultures supplemented with calcium or glycerophosphate alone. These results suggest that calcium glycerophosphate has unique properties that are more than the sum of its components.

In addition to ionic calcium and glycerophosphate, the compositions of the invention may further comprise at least one buffering agent to maintain the pH of the skin at a stable, normal level and to promote normal skin flora. Preferred buffering agents are α-hydroxy acids and more preferred are L-lactic acid and the D,L-lactic acid racemate since, as discussed previously, lactic acid has been shown to be effective in promoting keratinocyte differentiation and ceramide synthesis.

Figures 3, 4:
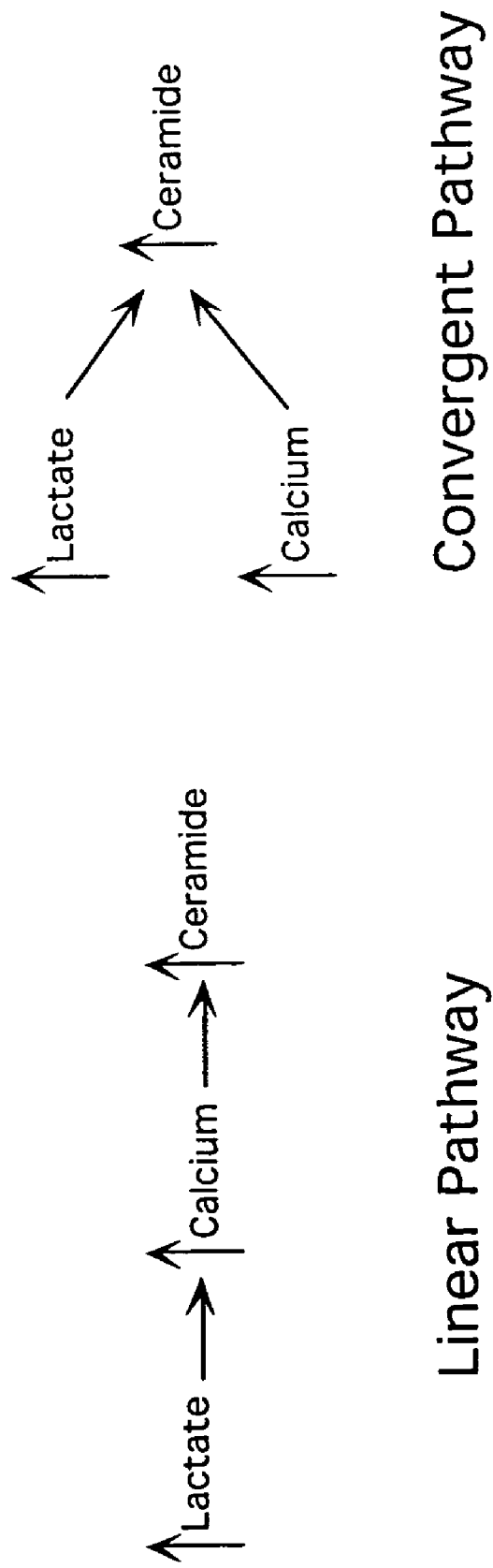
FIG. 3 is a diagram illustrating a linear reaction pathway between lactate and calcium.
FIG. 4 is a diagram illustrating a convergent reaction pathway between lactate and calcium.

It is not clear whether the preferred lactic acid and extracellular calcium act in a linear or convergent fashion, as best shown in FIGS. 3 and 4. However, while not wishing to be bound by theory, it appears that in either scenario, the effect of the two compounds may be at least additive, if not synergistic. Specifically, if lactate stimulates calcium uptake, an increase in extracellular calcium may maximize the effect of the lactate. However, if the two agents act by a convergent pathway, the effect of the simultaneous combination may be greater than the sum of the two when used separately.

A wide variety of ionic calcium-containing composition forms may be prepared according to the present invention. These include, but are not limited to, bar soaps, liquid soaps, shampoos, baths, creams, lotions, gels, ointments, powders such as talcum and baby powders and the like. All of these forms comprise, in addition to the ionic calcium, a dermatologically acceptable water-based, water-soluable or water miscible carrier. Additionally, the compositions according to the invention may be incorporated into a known skin moisturizer formulation, which would aid in producing moisturized skin that is thicker, more pliable and more youthful looking.

This invention further relates to a method for treating a skin condition of a mammal, such as dry skin, sunburn, other mild, first degree burns, dry scalp, or wounds, by applying to the skin of the mammal an effective amount of ionic calcium. In a preferred embodiment, the method further comprises applying to the skin effective amounts of α-hydroxy acid, preferably lactic acid, and glycerophosphate. The ionic calcium may be applied to an external surface of the skin and is preferably administered to the skin in an amount effective to improve the skin condition. Although any water soluble form of ionic calcium may be used according to the invention, it is preferred that the ionic calcium be applied as calcium glycerophosphate, particularly in view of its superior water solubility and superiority over calcium chloride as previously described. While not wishing to be bound by theory, it is believed that the ionic calcium improves the skin condition by stimulating of growth of new healthy skin cells which replace the damaged skin cells at a higher rate than under normal conditions.

Finally, a method for accelerating an internal cellular repair in a the skin of a mammal involves applying to the skin effective amounts of ionic calcium, an α-hydroxy acid and glycerophosphate. It is preferred that the calcium and glycerophosphate be applied in the form of CGP and that the α-hydroxy acid is lactic acid.

The method of applying ionic calcium as calcium glycerophosphate to the skin is highly advantageous because it is not likely to be accompanied by the adverse effects which sometimes occur with known products for skin treatment, such as retinoic acid. Retinoic acid stimulates keratinocyte differentiation, synthesis of collagen and elastin and promotes angiogenesis (formation of new blood vessels). While these actions thicken the stratum basale, they simultaneously thin the stratum corneum from its normal thickness of 14 cells to 5 cells (DiPiro, *Pharmacotherapy, A Pathophysiological Approach*, 4th edition, Appleton and Lange, page 1494 (1999)). The photosensitivity observed following retinoic acid treatment is likely a function of the chemical nature of retinoic acid itself: the retinoids are very efficient at absorbing UV light energy. The captured energy is dissipated to the surrounding tissues, with the effect that sunburn may be enhanced in susceptible individuals. Since calcium glycerophosphate absorbs UV light very poorly, it is unlikely that CGP would cause photosensitivity.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method for treating a condition of a skin of a mammal, wherein the condition is selected from the group consisting of dry skin, dry scalp, a sunburn, a burn, a minor irritation and a wound, the method comprising applying to the skin an effective amount of ionic calcium, at least one buffering agent to maintain the pH of the skin at a stable, normal level, wherein the at least one buffering agent comprises an α-hydroxy acid, and a glycerophosphate moiety.

2. The method according to claim 1, wherein the ionic calcium is applied to an external surface of the skin.

3. The method according to claim 1, wherein the ionic calcium is in a form of a water soluble organic or inorganic salt.

4. The method according to claim 3, wherein the water soluble organic salt is selected from the group consisting of calcium lactate, calcium citrate, calcium gluconate, calcium ascorbate, calcium acetate, calcium maleate, calcium pantothenate and calcium glycerophosphate.

5. The method according to claim 3, wherein the water soluble inorganic salt is selected from the group consisting of calcium carbonate and calcium chloride.

6. The method according to claim 1, wherein the α-hydroxy acid is selected from the group consisting of L-lactic acid and D,L-lactic acid racemate.

7. A method for accelerating an internal cellular repair in a skin of a mammal comprising applying to the skin effective amounts of ionic calcium, an α-hydroxy acid and a glycerophosphate moiety.

8. The method according to claim 7, wherein the α-hydroxy acid is selected from the group consisting of L-lactic acid and D,L-lactic acid racemate.

9. The method according to claim 7, wherein the ionic calcium is applied to an external surface of the skin.

10. The method according to claim 7, wherein the ionic calcium is in a form of a water soluble organic or inorganic salt.

11. The method according to claim 10, wherein the water soluble organic salt is selected from the group consisting of calcium lactate, calcium citrate, calcium gluconate, calcium ascorbate, calcium acetate, calcium maleate, calcium pantothenate and calcium glycerophosphate.

12. The method according to claim 11, wherein the water soluble organic salt comprises calcium glycerophosphate.

13. The method according to claim 10, wherein the water soluble inorganic salt is selected from the group consisting of calcium carbonate and calcium chloride.

* * * * *